(12) United States Patent
Sada et al.

(10) Patent No.: US 9,809,554 B2
(45) Date of Patent: Nov. 7, 2017

(54) PROCESS FOR PREPARING IVABRADINE

(71) Applicant: OLON S.p.A., Rodano (Milan) (IT)

(72) Inventors: Mara Sada, Segrate (IT); Faris Garis, Segrate (IT); Giorgio Bertolini, Segrate (IT)

(73) Assignee: OLON S.p.A., Rodano (Milan) (IT)

( * ) Notice: Subject to any disclaimer, the term of this patent is extended or adjusted under 35 U.S.C. 154(b) by 0 days.

(21) Appl. No.: 14/892,771

(22) PCT Filed: May 19, 2014

(86) PCT No.: PCT/IB2014/000762
§ 371 (c)(1),
(2) Date: Nov. 20, 2015

(87) PCT Pub. No.: WO2014/188248
PCT Pub. Date: Nov. 27, 2014

(65) Prior Publication Data
US 2016/0107998 A1    Apr. 21, 2016

(30) Foreign Application Priority Data
May 22, 2013  (IT) ............... MI2013A0830

(51) Int. Cl.
*C07D 223/16*   (2006.01)
*B01J 23/44*    (2006.01)
(52) U.S. Cl.
CPC ............ *C07D 223/16* (2013.01); *B01J 23/44* (2013.01)

(58) Field of Classification Search
CPC .............................. C07D 223/16; B01J 23/44
See application file for complete search history.

(56) References Cited

U.S. PATENT DOCUMENTS 5,296,482 A    3/1994   Peglion et al.

FOREIGN PATENT DOCUMENTS

| EP | 0 534 859      | 3/1993  |
|----|----------------|---------|
| WO | WO 2008/146308 | 12/2008 |
| WO | WO 2011/138625 | 11/2011 |
| WO | WO 2013/024400 | 2/2013  |
| WO | WO 2014/114341 | 7/2014  |

OTHER PUBLICATIONS

IUPAC Gold Book, Compendium of Chemical Terminology 2.3.3 Feb. 24, 2014; excerpt p. 1-3.*
Stevens, G.W., Kirk Othmer Encyclopedia of Chemcial Technology, Liquid-Liquid Extraction Jun. 15, 2007; p. 1-62.*
International Search Report for PCT/IB2014/000762 mailed Aug. 5, 2014, three pages.
International Preliminary Report on Patentability for PCT/IB2014/000762 mailed May 11, 2015, six pages.
IT Search Report for MI20130830 dated Oct. 14, 2013, two pages.

* cited by examiner

*Primary Examiner* — Matt Mauro
(74) *Attorney, Agent, or Firm* — Nixon & Vanderhye P.C.

(57) ABSTRACT

The invention refers to a process for preparing ivabradine, in particular a process for preparing an ivabradine salt.

9 Claims, No Drawings

PROCESS FOR PREPARING IVABRADINE

This application is the U.S. national phase of International Application No. PCT/IB2014/000762 filed 19 May 2014 which designated the U.S. and claims priority to IT Patent Application No. MI2013A000830 filed 22 May 2013, the entire contents of each of which are hereby incorporated by reference.

SUMMARY OF THE INVENTION

The present invention refers to a process for preparing ivabradine, in particular a process for preparing an ivabradine salt.

TECHNICAL FIELD

Ivabradine or 3-[3-({[(7S)-3,4-dimethoxybicyclo[4.2.0]octa-1,3,5-trien-7-yl]methyl}(methyl)amino)propyl]-7,8-dimethoxy-1,3,4,5-tetrahydro-2H-3-benzazepin-2-one has the following formula

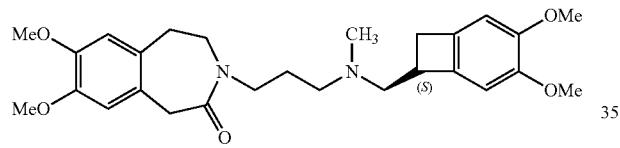

and is used in cardiology against heart failure, hypertension, angina and for the post-infarction treatment.

Ivabradine has been described for the first time in patent EP 0 534 859 in the name of Adir/Servier. In such a document, ivabradine hydrochloride was prepared by hydrogenation of the 3-[3-[[[(7S)-3,4-dimethoxybicyclo[4.2.0]octa-1,3,5-trien-7-yl]methyl]methylamino]propyl]-1,3-dihydro-7,8-dimethoxy-2H-3-benzazepin-2-one compound (hereinafter also dehydro-ivabradine) and further reaction of basic ivabradine with hydrochloric acid.

This process has the disadvantage of starting from a dehydro-ivabradine that has to be purified before the hydrogenation reaction otherwise the result thereof, in terms of yield and purity of the final compound, is not acceptable.

WO2011/138265 describes a process for preparing ivabradine wherein a salified dehydro-ivabradine is prepared, which is desalified and then reduced with gaseous hydrogen in an acid environment to give an ivabradine salt. As can be seen from the examples, in particular from example 16 of WO2011/138265, the dehydro-ivabradine oxalate is desalified with aqueous potassium carbonate and the obtained compound is then purified by distillation and treatment with methanol, then it is reduced in an aqueous hydrochloric acid solution.

WO2008/146308 describes a process for preparing ivabradine hydrochloride starting from not-salified dehydro-ivabradine. The described process provides for many extraction steps that are needed to remove impurities from the product but, at the same time, they inevitably reduce the yields (that in fact are never reported). In example 3, that provides the best purity, further steps of salification of ivabradine with an organic acid, purification of said organic salt, hydrolysis and salification with hydrochloric acid, are also introduced. It is clear that all these additional steps are directed to the removal of impurities from ivabradine but inevitably reduce the yields.

There is the need of providing new methods for preparing ivabradine with a high purity level and good yields that allow to avoid the excessive purification of the initial dehydro-ivabradine, that simplify the synthesis by limiting the reaction steps, thus avoiding the drawbacks of the prior art.

OBJECTS OF THE INVENTION

It is an object of the invention to provide an alternative process to synthesize ivabradine, in particular an ivabradine salt, even more in particular ivabradine hydrochloride.

It is a further object of the invention to provide a process to synthesize ivabradine, in particular ivabradine hydrochloride, that is industrially convenient and that provides the desired compound having excellent yields and a suitable purity.

DESCRIPTION OF THE INVENTION

Now it has been unexpectedly found that, by salifying dehydro-ivabradine with hydrochloric acid, a compound with high purity level is obtained that simplifies the subsequent hydrogenation reaction and allows to obtain the corresponding ivabradine hydrochloride in a very pure form and with excellent yields.

Dehydro-ivabradine hydrochloride salt has not been selected randomly. In fact several inorganic and organic salts have been tested, but no one of the tested salts has provided the excellent results provided by the hydrochloride salt, in terms of yields, purity and ease of operation.

Furthermore, the use of dehydro-ivabradine hydrochloride allows to directly obtain, after the last reaction, the molecule in the current commercial form thereof, without therefore the need of carrying out further unblocking, salification and purification steps.

Therefore, according to one of its aspects, the present invention has the object of a process for preparing the ivabradine hydrochloride salt of formula (I)

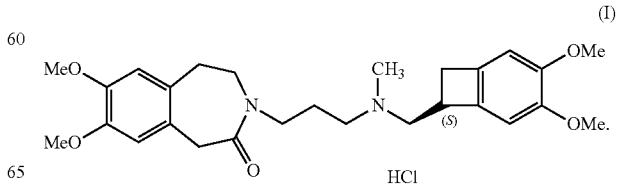

comprising hydrogenating 3-[3-[[[(7S)-3,4-dimethoxybicyclo[4.2.0]octa-1,3,5-trien-7-yl]methyl]methylamino]propyl]-1,3-dihydro-7,8-dimethoxy-2H-3-benzazepin-2-one hydrochloride (dehydro-ivabradine hydrochloride) in a suitable solvent.

If desired, the ivabradine salt obtained with the process of the invention, can be converted into ivabradine by hydrolysis, according to conventional techniques.

The initial dehydro-ivabradine salt is the hydrochloride but, if desired or needed, also the hydrobromide salt can be used to get the ivabradine hydrobromide that, if desired or needed, can be easily converted into basic ivabradine, or into ivabradine hydrochloride, according to methods well known to a person skilled of the art.

The hydrogenation of the present invention can be carried out with any reducing reagent known to a person skilled of the art.

According to an advantageous embodiment, the hydrogenation of the invention is carried out with gaseous hydrogen.

According to another embodiment of the invention, the hydrogenation is carried out with gaseous hydrogen in a solvent or in a solvent mixture, e.g. in a solvent selected among alcohols or mixtures thereof, advantageously lower C1-C4 alcohols, such as for example methanol, ethanol, isopropanol, preferably methanol.

When the hydrogenation of the invention is carried out with gaseous hydrogen, it is preferably done in presence of a catalyst such as for example Pd/C, or other catalysts usually employed in reductions with gaseous hydrogen.

The hydrogenation reaction with gaseous hydrogen, a solvent and a catalyst like those described above, is generally carried out at a temperature between room temperature and 60° C., conveniently around 20-40° C., e.g. 30-35° C. It is in fact convenient to keep the reaction temperature low so as to avoid the formation of byproducts.

The reaction mixture has not acidic pH and the reaction occurs easily and is completed in few hours, for example in 10-20 hours depending on the amount of reagents and the reaction temperature. The person skilled of the art can clearly follow the evolution thereof with common methods, e.g. by means of thin film chromatography (TLC) or HPLC.

Advantageously, the reaction occurs in a hydrogen atmosphere, upon inertization in order to remove all the oxygen present. According to a preferred embodiment, the reaction is carried out at 4-5 bars.

At the end of the reaction, the catalyst is removed, e.g. by filtration and the solvent is evaporated.

The ivabradine hydrochloride is directly obtained with excellent yields and high purity, usually greater than 99.5%. However, if desired, it is possible to further purify the compound by grinding it with a suitable solvent, e.g. acetonitrile, acetone, ethyl acetate, or by crystallizing it e.g. from acetonitrile, acetone or isopropanol.

Dehydro-ivabradine hydrochloride can be prepared from dehydro-ivabradine by reacting with hydrochloric acid, according to methods known in the art.

The use of 3-[3-[[[(7S)-3,4-dimethoxybicyclo[4.2.0]octa-1,3,5-trien-7-yl]methyl]methylamino]propyl]-1,3-dihydro-7,8-dimethoxy-2H-3-benzazepin-2-one hydrochloride (dehydro-ivabradine hydrochloride) for preparing ivabradine represents another aspect of the present invention.

Details of the reactions of the process of the invention are provided in the experimental section of the present description. Comparative examples are also provided wherein other dehydro-ivabradine salts are reduced, in particular oxalate and tartrate, however obtaining inadequate results.

In particular, for the oxalate salt it has been observed that before the hydrogenation reaction a further purification is needed to obtain an at least acceptable purity, with a resulting yield loss; moreover, it has been observed that even with the use of a purified starting oxalic salt, during hydrogenation of such a salt there is a greater formation of byproducts as a consequence of the high temperatures at which the reaction is carried out.

As regards the tartrate salt, said salt is obtained with high yields but also in this case in a low purity form; moreover said salt is not easily recrystallizable and for the crystallization 40-50 volumes of solvent are required, being this condition clearly not acceptable from an industrial point of view.

EXPERIMENTAL SECTION

Example 1

Preparation of Dehydro-Ivabradine

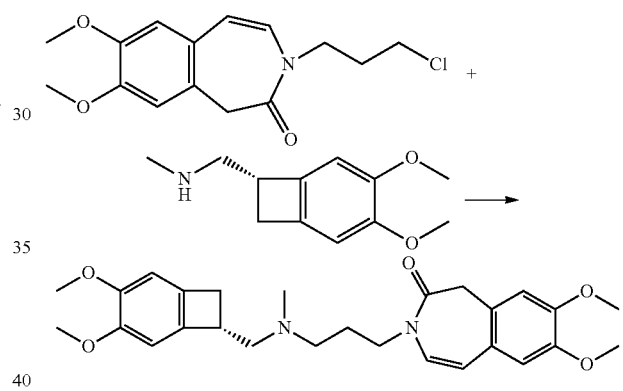

| Reagents | Grams | Moles | Equiv. |
|---|---|---|---|
| 3-(3-chloropropyl)-7,8-dimethoxy-1,3-dihydro-2H-3-benzazepin-2-one Mw = 295.76 g/mol | 364 g | 1.23 | 1 |
| (1S)-4,5-Dimethoxy-1-[(methylamino)methyl]benzocyclobutane Mw = 207.27 g/mol | 280 g (254.9 g theoretical) | 1.23 | 1 |
| Potassium Carbonate Mw = 138.2 g/mol | 170 g | 1.23 | 1 |
| Potassium Iodide Mw = 166.0 g/mol | 31.4 g | 0.189 | 0.15 |
| Methylisobutylketone (MIBK) (of which 1000 ml for the amine) | 3600 ml | — | — |
| Water | 1000 ml | — | — |
| Water | 500 ml | — | — |
| Water | 1500 ml | — | — |
| HCl 33% w/w | 120 g | 1.1 | |
| Methylisobutylketone (MIBK) | 5 × 300 ml (tot 1.5 l) | — | — |
| Methylisobutylketone (MIBK) | 800 ml | — | — |
| NaOH 30% w/w | 143 g | 1.1 | — |
| Water | 500 ml | — | — |

In a 6 l multiple neck flask under nitrogen atmosphere 364 g of 3-chloropropyl-4,5-dimethoxybenzazepinone, 170 g of potassium carbonate, 31.4 g of potassium iodide and 2600 ml of MIBK are sequentially loaded. The unblocked amine dissolved in the remaining MIBK (1000 ml) is added and the reaction is heated to 85-90° C. The reaction is left under stirring while heating for 48 hours, controlling it by TLC and HPLC. Next the mixture is cooled to 60-70° C. and the organic phase is washed 2 times with 1000 ml and 500 ml of water. The organic phase is acidified with 33% w/w HCl keeping the temperature around 40° C. The organic phase is removed and the aqueous phase containing the product is washed with 1.5 l of MIBK (5×300 ml) keeping the temperature around 40° C. 800 ml of MIBK are added, and the mixture is basified with 143 g of 30% NaOH. The aqueous phase is eliminated, the organic phase is washed with $H_2O$, MIBK is dried and concentrated until dryness obtaining 537 g of oil.

Crude yield: 93%
(LC-MS: $MH^+$=467)

Example 2

Preparation of Dehydro-Ivabradine Hydrochloride (II)

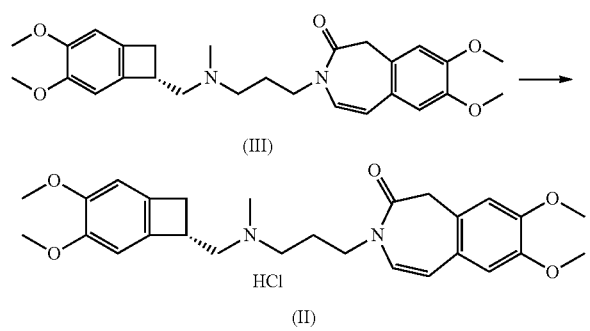

| Reagents | Grams | Moles | Equiv. |
|---|---|---|---|
| Dehydro-ivabradine Mw = 466.57 | 537 g | 1.15 | 1 |
| Acetonitrile | 1000 ml | — | — |
| Acetonitrile | 2800 ml | — | — |
| $Na_2SO_4$ | a.n. | — | — |
| 4.5% HCl solution in acetonitrile | 1160 g | 1.43 | 1.25 |
| Acetonitrile | a.n. | — | — |

Dehydro-ivabradine (III) is mixed with 1000 ml of acetonitrile and evaporated until dryness. It is taken up with 2800 ml of acetonitrile and the solution dried with $Na_2SO_4$. 1160 g of an acetonitrile solution containing 4.5% w/w HCl are added dropwise and, while keeping the temperature not above 20-25° C., the primer is added halfway of the dropwise addition. The mixture is cooled and the salt is left to cold crystallize at 0-5° C. for about 24 hours. By washing with a little of cold acetonitrile, 430 g of the title compound is obtained.

Yield: 74%
(LC-MS: $MH^+$=467, $MNa^+$=489)
$H^1$NMR (DMSO-d6): 1.90 (2H); 2.72 (3H); 2.75-2.90 (1H); 2.90-3.05 (2H); 3.05-3.25 (2H); 3.38 (2H); 3.52 (2H); 3.62 (2H); 3.70 (9H); 3.75 (3H); 6.45 (2H); 6.75 (1H); 6.83 (1H); 6.89 (1H); 6.93 (1H); 10.6 (1H).

Example 3

Preparation of Ivabradine Hydrochloride

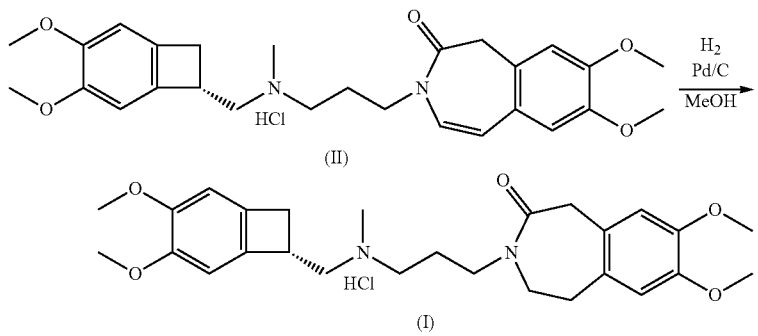

| Reagents | Grams | Moles | Equivalents |
|---|---|---|---|
| Dehydro-ivabradine HCl Mw = 503.03 | 50 g | 0.099 | — |
| Pd/C 5% (50% wet) | 5 g | — | — |

50 g of dehydro-ivabradine hydrochloride (II) are dissolved in 500 ml of methanol and loaded into the autoclave previously inertized with nitrogen. 5 g of catalyst are added and hydrogen is loaded at a pressure of 4-5 bars. The reaction is left at 30-35° C. for about 18 hours. The disappearance of the starting material is checked with TLC or HPLC. The solvent is evaporated under reduced pressure until dryness, the residue is taken up with 150 ml of acetonitrile and the solvent is again removed under reduced pressure. The residue is taken up with 1250 ml of acetonitrile to carry out the crystallization of the desired compound with a HPLC purity greater than 99.5%.

Yield 80%.

Example 4

Crystallization of Ivabradine Hydrochloride 40 g of ivabradine hydrochloride (I) are dissolved in 1000 ml of acetonitrile. The wet product is washed over a panel with 200 ml of acetone. The product is ground in acetone at room temperature for about 1 hour. It is filtered, further washed with 400 ml of acetone and dried at 60° C. for about 24 hours to give the title compound with a HPLC purity greater than 99.9%.

(LC-MS: $MH^+$=469)
$H^1$NMR ($D_2O$): 2.05 (2H); 2.62 (1H); 2.85 (3H); 2.95 (2H); 3.05 (2H); 3.1-3.2 (2H); 3.35 (1H); 3.5-4.00 (7H); 3.55 (3H); 3.72 (3H); 3.76 (3H); 3.88 (3H); 6.58 (1H); 6.65 (2H); 6.73 (1H).
$C^{13}$ NMR: 23.1, 31.5, 34.9, 37.0, 40.5, 40.9, 44.0, 47.1, 51.8, 55.4, 56.0, 59.4, 106.9, 107.8, 113.5, 113.6, 123.1, 127.8, 134.9, 146.4, 147.3, 148.6, 149.7, 176.4.

Comparative Example A

A'—Preparation of Dehydro-Ivabradine Oxalate

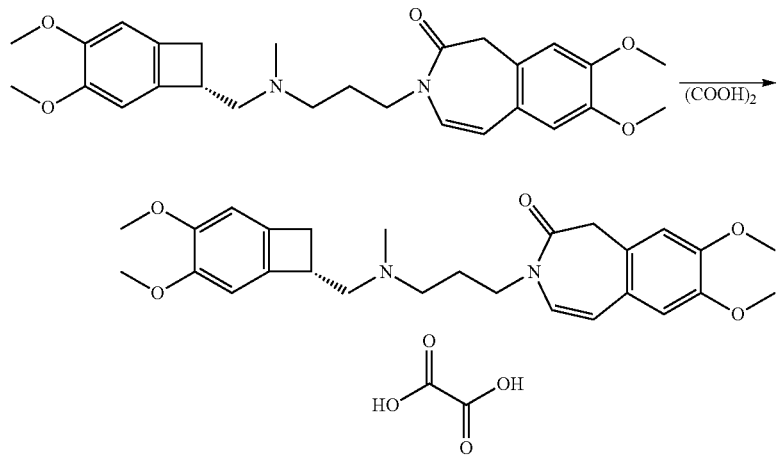

| Reagents | Grams | Moles | Equiv. |
|---|---|---|---|
| Dehydro-ivabradine Mw = 466.57 | 620 g | 1.33 | 1 |
| Methanol | 1240 ml | — | — |
| Methanol | 6760 ml | — | — |
| Oxalic acid dihydrate Mw = 126.0 | 168 g | 1.33 | 1 |
| Methanol | 500 ml | — | — |

In a reactor 168 g of oxalic acid dihydrate are dissolved in 6760 ml of methanol, the mixture is heated to 45-50° C. until complete dissolution. A solution of 620 g of dehydro-ivabradine (III) in 1240 ml of methanol is added and it is left at a temperature (45-50° C.) for about 1 hour. A primer of dehydro-ivabradine oxalate is added and the mixture is left to recover at room temperature. Next it is cooled to 0-5° C. for 1 hour and the product is filtered. The white solid is washed on a panel with 500 ml of methanol and recrystallized by dissolving it in 13 volumes of methanol. 465 g of dehydro-ivabradine oxalic salt are obtained.

Yield: 63%

(LC-MS: MH$^+$=467)

A"—Hydrogenation of Dehydro-Ivabradine Oxalate

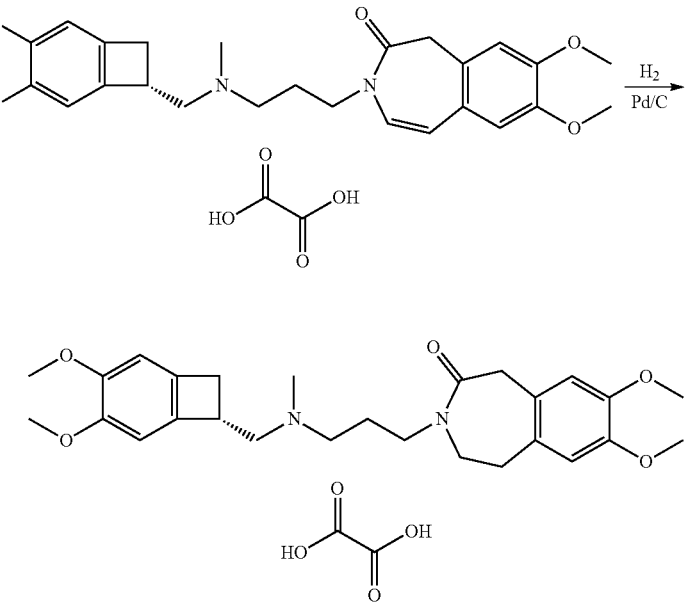

| Reagents | Grams | Moles | Equiv. |
|---|---|---|---|
| Dehydro-ivabradine oxalic salt Mw = 556.60 | 10 g | 0.018 | 1 |
| Methanol | 200 ml | — | — |
| Pd/C 5% (50% wet) | 0.8 g | | |
| Methanol | 20 ml | — | |
| Isopropanol | 100 ml | | — |
| Isopropanol | 10 ml | | |

10 g of dehydro-ivabradine oxalic salt, 200 ml of methanol and 0.8 g of catalyst are loaded in an autoclave previously inertized with nitrogen. Hydrogen is loaded up to a pressure of 5 bars and the reaction mixture is heated to 55-60° C. The reaction evolution is checked by means of HPLC or TLC.

After about 7 hours the reaction is completed. The autoclave is unloaded, the catalyst is filtered on a celite panel and the panel is washed with 20 ml of methanol. The filtrate is evaporated under reduced pressure and 100 ml of isopropanol are added while heating the mixture to 40-45° C. for about 1 hour. It is left to recover at 20° C. and the obtained solid is filtered. 7.7 g of ivabradine oxalic salt are obtained.

HPLC purity: 98.5%

Yield: 77%

(LC-MS: $MH^+$=469)

Comparative Example B

B'—Preparation of Dehydro-Ivabradine L-Tartrate

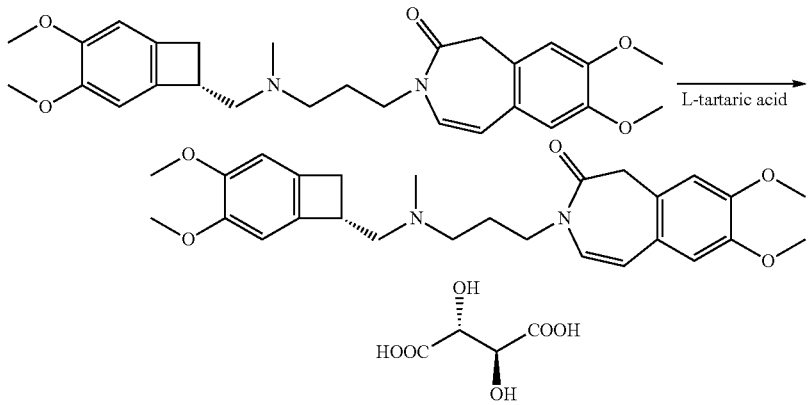

| Reagents | Grams | Moles | Equiv. |
|---|---|---|---|
| Dehydro-ivabradine Mw = 466.57 | 24 g | 0.05 | 1 |
| MIBK | 960 ml | — | — |
| L-tartaric acid Mw = 150.09 | 8.2 g | 0.05 | 1 |
| Acetone | 164 ml | | |
| MIBK | 80 ml | — | — |
| Acetone | 40 ml | | |

24 g of dehydro-ivabradine dissolved in 960 ml of MIBK are charged in a flask. A solution of 8.2 g of L-tartaric acid in 164 ml of acetone is added dropwise and left under stirring for about 1 hour. The precipitate is filtered and washed with a solvent mixture made of 80 ml of MIBK and 40 ml of methanol. 26 g dry are obtained.

Yield: 84%

(LC-MS: $MH^+$=467)

B"—Hydrogenation of Dehydro-Ivabradine L-Tartrate

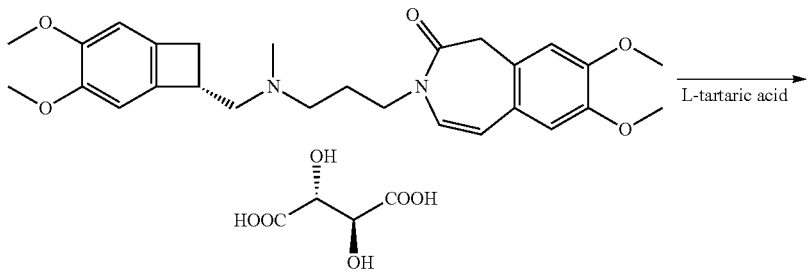

-continued

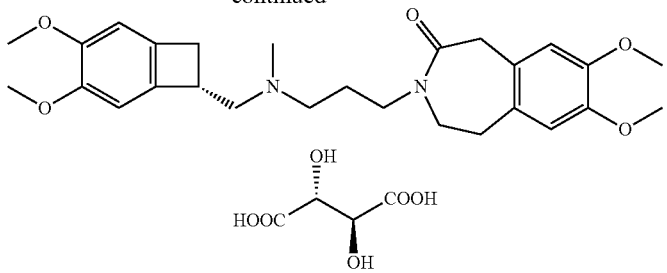

| Reagents | Grams | Moles | Equiv. |
|---|---|---|---|
| dehydro-ivabradine L-tartrate Mw = 616.66 | 17 g | 0.027 | |
| Methanol | 225 ml | | |
| Pd/C 5% (50% wet) | 1.7 g | | |
| Methanol | 30 ml | | |
| Ethyl acetate | 30 ml | | |
| Ethyl acetate | 10 ml | | |

17 g of dehydro-ivabradine L-tartaric salt, 255 ml of methanol and 1.7 g of catalyst are loaded in an autoclave previously inertized with nitrogen. Hydrogen is loaded up to a pressure of 5 bars and the reaction mixture is heated to 35-40° C. The reaction evolution is checked by means of HPLC or TLC.

After about 22 hours the reaction is completed. The autoclave is unloaded, the catalyst is filtered on a celite panel and the panel is washed with 30 ml of methanol.

The filtrate is evaporated under reduced pressure and the solid is taken up with 30 ml of ethyl acetate. The mixture is heated to 30-35° C., after 1 hour it is recovered at room temperature and the solid is filtered. The product is washed on a filter with 10 ml of ethyl acetate and the product id dried. 12 g of ivabradine L-tartaric salt are obtained.

Yield: 72%

HPLC purity: 98.9%

(LC-MS: MH$^+$=469)

As can be noted, with respect to the results obtained with the hydrochloride salt, the reactions reported in the comparative examples provided, in addition to a lower yield, also a lower purity of the compounds (as measured by HPLC). A person with ordinary skill in the art knows well that, in pharmaceutical field, very high values of purity are requested and therefore even one percentage point of purity (as measured by HPLC) is considered extremely important for such compounds, which could not otherwise be used as such but should undergo repeated purifications until they achieve the purity requested by pharmaceutical standards, resulting in an increase of working loads and industrial production costs.

The invention claimed is:

1. A process for preparing ivabradine hydrochloride of formula (I)

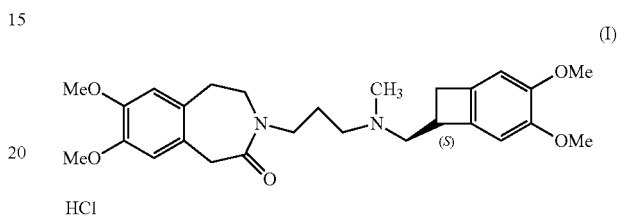

(I)

comprising
a) reacting 3-(3-chloropropyl)-7,8-dimethoxy-1,3-dihydro-2H-3-benzazepin-2-one with (1S)-4,5-dimethoxy-1-[(methylamino)methyl] benzocyclobutane in suitable solvent;
b) reacting the 3-[3-[[[(7S)-3,4-dimethoxybicyclo[4.2.0] octa-1,3,5-trien-7-yl]methyl]methylamino]propyl]-1,3-dihydro-7,8-dimethoxy-2H-3-benzazepin-2-one obtained in step a) with HCl in a suitable solvent to obtain 3-[3-[[[(7S)-3,4-dimethoxybicyclo[4.2.0]octa-1,3,5-trien-7-yl]methyl]methylamino]propyl]-1,3-dihydro-7,8-dimethoxy-2H-3-benzazepin-2-one hydrochloride;
c) further obtaining 3-[3-[[[(7S)-3,4-dimethoxybicyclo[4.2.0]octa-1,3,5-trien-7-yl]methyl]methylamino]propyl]-1,3-dihydro-7,8-dimethoxy-2H-3-benzazepin-2-one hydrochloride obtained in step b) as a solid hydrochloride salt;
d) dissolving the solid hydrochloride salt from step c) in a C1-C4 alcohol solvent; and
e) hydrogenating the dissolved 3-[3-[[[(7S)-3,4-dimethoxybicyclo[4.2.0]octa-1,3,5-trien-7-yl]methyl]methylamino]propyl]-1,3-dihydro-7,8-dimethoxy-2H-3-benzazepin-2-one hydrochloride to obtain the compound of formula (I).

2. The process according to claim 1, wherein said hydrogenating is carried out with gaseous hydrogen.

3. The process according to claim 2, wherein said suitable solvent in step a) is methylisobutylketone.

4. The process according to claim 3, wherein said C1-C4 alcohol is methanol.

5. The process according to claim 1, wherein the hydrogenating is carried out in the presence of a catalyst.

6. The process according to claim 5, wherein said catalyst is Pd/C.

7. The process according to claim 1, wherein the reaction of step a) is carried out at a temperature between 20 and 40° C.

8. The process according to claim 1, wherein said suitable solvent in step a) is methylisobutylketone.

9. The process according to claim 8, wherein said C1-C4 alcohol is methanol.

* * * * *